United States Patent [19]

Leonard, Jr.

[11] 4,343,848
[45] Aug. 10, 1982

[54] EMBOSSED THERMOPLASTIC MATERIAL

[75] Inventor: Erving A. Leonard, Jr., Terre Haute, Ind.

[73] Assignee: Ethyl Corporation, Richmond, Va.

[21] Appl. No.: 216,127

[22] Filed: Dec. 15, 1980

[51] Int. Cl.³ ........................... B32B 3/30; B32B 3/28
[52] U.S. Cl. .................................. 428/156; 428/167; 428/174; 428/179; 428/332; 428/337
[58] Field of Search ............... 428/156, 167, 174, 179, 428/180, 332, 337; 264/284; 24/16 PB

[56] References Cited

U.S. PATENT DOCUMENTS

| | | | |
|---|---|---|---|
| Re. 23,910 | 12/1954 | Smith et al. | 18/19 |
| 3,137,746 | 6/1964 | Seymour et al. | 264/73 |
| 3,484,835 | 12/1969 | Trounstine et al. | 264/284 |
| 3,760,940 | 9/1973 | Bustin | 206/58 |
| 3,911,187 | 10/1975 | Raley | 428/179 |

*Primary Examiner*—Paul J. Thibodeau
*Attorney, Agent, or Firm*—Donald L. Johnson; John F. Sieberth; Paul H. Leonard

[57] ABSTRACT

An embossed thermoplastic film characterized in that one surface of the film is provided with a plurality of rows of protuberances having the shape of pyramids with square bases which extend perpendicular to both the longitudinal and the transverse axes of the film. The protuberances are joined at the edge of the bases by flat valley portions which intersect each other at right angles. The embossed film has a low coefficient of friction and increased embossed thickness.

7 Claims, 3 Drawing Figures

EMBOSSED THERMOPLASTIC MATERIAL

BACKGROUND OF THE INVENTION

This invention relates to embossed thermoplastic materials, particularly to flexible, embossed thermoplastic films suitable for use in a variety of applications.

Embossed plastic film or sheet material has come into widespread use in many fields. One particularly large-scale use of embossed thermoplastic sheet material is that of disposable articles such as hospital pads and drapes, wearing apparel and disposable diapers. Embossed film is also finding increased use in the packaging field, for example, as bags and overwraps for articles such as clothing, etc., and for shopping bags. In order to fulfill the requirements established by a large number of end uses of embossed film, it is desirable that the film have a low coefficient of friction when run through fabricating machines, particularly those used for manufacture of disposable clothing articles such as diapers. In some cases, it is important that the embossed thermoplastic film be very soft and flexible and have the proper pattern and embossment depth in order to provide the desired "hand" or clothlike feel for the thermoplastic embossed material. Additionally, for many uses it is desired that the embossed thermoplastic material have as low a surface gloss as possible to order to simulate woven clothlike fabrics. Further, embossed thermoplastic materials must meet the minimum physical requirements necessary for the films to be handled in high speed, automatic, fabricating machinery, i.e., it should have suitable modulus, tensile strength, and impact strength.

Embossed film having a truncated pyramid pattern wherein the valleys separating the pyramids are continuous over the full length and width of the film is shown in U.S. Pat. No. 3,760,940. Examples of embossed film having a pattern of rounded top, rectangular base protuberances wherein the valleys extend perpendicular to the transverse and longitudinal axes of the film is shown in U.S. Pat. No. 3,484,835. Square pattern film produced by embossing on a traveling wire wherein the valleys extend parallel to the longitudinal and transverse axes of the film is shown in U.S. Pat. No. Re. 23,910. U.S. Pat. No. 3,137,746 discloses a film having a hexagonal, raised pattern on one surface thereof which is subsequently oriented and slit between the embossments to produce a porous film. The hexagons are initially arranged so that continuous valleys exist on two opposite sides of the individual rows of protuberances.

Embossing patterns as shown in the foregoing patents produce embossed film which have a high coefficient of friction. In some applications such as baby diapers, it is desirable that the coefficient of friction be kept low.

SUMMARY OF THE INVENTION

An embossed thermoplastic film characterized in that one surface of the film is provided with a plurality of rows of protuberances having the shape of pyramids with square bases which extend perpendicular to both the longitudinal and the transverse axes of the film. The protuberances are joined at the edge of the bases by flat valley portions which intersect each other at right angles. The embossed film has a low coefficient of friction and increased embossed thickness.

One of the advantages of the film of the present invention is that the film has a low coefficient of friction.

A low coefficient of friction permits the film to be easily processed on diaper manufacturing machines.

An additional advantage of the film of the present invention is that the film has an increased embossed thickness over prior art film. An increased embossed thickness greatly improves handling of the film on processing machinery, and in particular, rolling up the film on large storage rolls.

DESCRIPTION OF THE PREFERRED EMBODIMENTS

Figure 1:
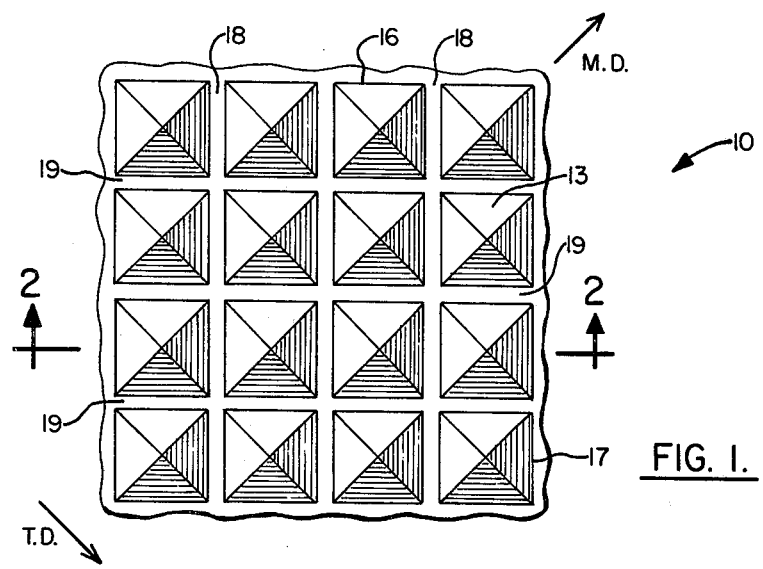
FIG. 1 is a top plan view of the male surface of the embossed thermoplastic sheet of the present invention.

Referring now to FIG. 1, there is seen a portion of a thermoplastic embossed sheet of film of the present invention designated generally by the numeral 10. The film has an upper surface designated by the numeral 13 and a lower surface designated by the numeral 14.

The portion of embossed film shown in FIG. 1. has been produced by feeding a continuous length of film into the nip of an embossing roll along the machine or longitudinal direction as indicated by the arrow marked "MD". The machine direction is generally parallel to the diagonal of the base of the pyramids and the arrow "MD" forms an angle of about 45 degrees with rows of embossments 16 and 17. The transverse direction is marked by the arrow with the legend "TD".

Figure 2:
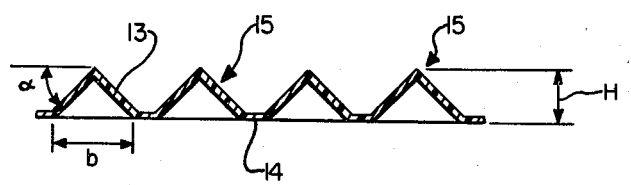
FIG. 2 is a cross-sectional view of the film along line 2—2 of FIG. 1.

As seen more clearly in FIG. 2, the embossed film of this invention is provided with a plurality of pyramid-shaped protuberances designated generally by the numeral 15, all of which extend upwardly out of the plane of the film from its upper surface 13. The protuberances are pyramid-shaped. As noted, the protuberances are arranged in rows 16 and 17. Rows 16 are perpendicular to rows 17. The series of adjacent rows of protuberances 16 are separated by continously extending flat valleys or depressions 18 over the entire length of the film. The rows 17 which extend across the film 10 are defined by a series of flat valleys 19.

Figure 3:
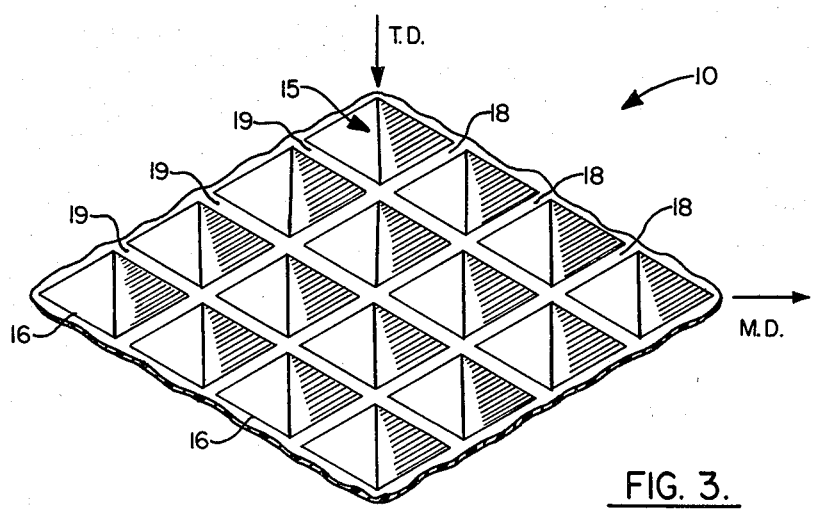
FIG. 3 is a perspective view of the top or the male surface of the thermoplastic embossed film of the present invention.

As seen more clearly in FIG. 2, each protuberance 15 has a height indicated by the letter "H". The protuberances all extend upwardly out of the plane of the film as seen more clearly in FIGS. 2 and 3. The sides 20 of the protuberances are inclined at an angle "alpha" to the plane of the film. This angle may be from about 20 degrees to about 75 degrees. Preferably, this angle is about 45 degrees. The protuberances generally may have a base width "b" of from about 4 mils to about 10 mils. The protuberances have a height "H" of from about ½ mil to about 4 mils. In general, the embossed films of this invention are prepared from thermoplastic films having an initial thickness of from about 0.5 mil to about 10 mils.

The embossed film of the present invention can be prepared from any suitable thermoplastic material, particularly the homopolymers and copolymers of alpha-olefins having 2 to 4 carbon atoms, e.g., medium, low, and high density polyethylene, polypropylene, polybutyene-1, and copolymers thereof with each other and with other polymerizable comonomers. Also suitable are films made from polymerized and copolymerized vinyl monomers such as polyvinyl chloride, polyvinylidene chloride, polystyrene, and other such type films. Other films that may be embossed include polyethylene terephthalate (Mylar), polyvinyl acetate, polyvinyl alcohol, Nylon and other polyamides, cellulosics such as cellulose acetate and butyrate, styrene-nitrile type copolymers and graft polymers. Additionally, embossed films may be made from multilayer films, for example, films such as polyethylene:Nylon, HDPE:LDPE:HDPE, LDPE:polyvinyl acetate:LDPE, LDPE:polypropylene:LDPE, and others.

The embossed film of the present invention may be prepared by any suitable means by utilizing a preformed web of film and passing it between embossing rollers, or extruding molten thermoplastic from a slot die directly into the nips of a pair of embossing rollers. If preformed film is used, the film is heated by any suitable heating means (not shown) to a suitable temperature for embossing prior to entering the nip of the embossing rolls. One embossing roll may be a hollow steel cylinder having the truncated pyramid pattern described above engraved on its surface to provide an inwardly extending protuberance or female pattern on the cylindrical surface of the roll. The female pattern on the embossing roll is preferably produced by intaglio etching. The other roll may be provided with a resilient rubber covering, i.e., a neoprene or silastic rubber, preferably having a hardness of about 35 Durometer to about 95 Durometer, and is pressed against the embossing roll by suitable means (not shown) to apply pressure of from about 50 pounds per lineal inch to about 500 pounds per lineal inch between the nips of the rolls. Preferably, one or both of the embossing rolls are hollow and are provided with conduit means (not shown) whereby a cooling fluid may be circulated through one or both rolls to chill the film and to set the embossed pattern into the film before it leaves the rolls. After passing from the embossing roll, the embossed film 10 is then wound onto a storage roll which may be packaged and sold as is or may be subsequently slit into a smaller diameter and shorter length rolls for subsequent sale.

While it is preferred to use a single embossed metal roller and a rubber covered backup roller to produce the film of the present invention, the film may also be produced by feeding the heated film into the nips of a pair of matched, engraved rollers, i.e., one roller having a raised embossment on its surface and the other roller having a matching depressed engraving adapted to match and receive the raised embossments on the other roller. Prior to introduction of the unembossed web 21 into the embossing rollers, the web may be heated by any suitable means (not shown), e.g., by being passed between infrared radiant heaters or gas powered radiant heaters, by passage through hot air ovens, by passage over heated metal rollers, or any other suitable means, in order to raise the temperature of the film to that which is suitable for providing a deep and sharp impression when it is received in the nip of the embossing rollers.

Polyethylene film was embossed with an embossing roll prepared by sandblasting the surface thereof with 120 grit sand to form a rough embossing surface thereon. Approximately 2,000 samples were taken from the prepared film. The average coefficient of friction in accordance with ASTM D-1894 of the approximately 2,000 samples was 1.2, and the coefficient of friction range was from 1.1 to 1.3.

The same formulation of polyethylene film was then embossed using an embossing roll having the pyramidal configuration of the invention engraved therein. Approximately 2,000 runs were made with the average coefficient of friction in accordance with ASTM D-1894 of the samples being 0.8, and the coefficient of friction range was from 0.5 to 0.9.

It is thus seen that the coefficient of friction of film prepared in accordance with the present invention is much less than typical embossed film. Such a significant decrease in coefficient of friction allows the film to be processed much more easily on embossing equipment.

Although the preferred embodiments of the present invention have been disclosed and described in detail above, it should be understood that the invention is in no sense limited thereby and its scope is to be determined by that of the following claims.

What is claimed:

1. An embossed length of thermoplastic film, said film having a plurality of rows of pyramid-shaped protuberances intersecting the longitudinal and transverse axis of said length of film at an angle of about 45 degrees, the rows of protuberances aligned with one each of said axes being separated by continuous flat valleys extending from one side of said film to the other side of said film.

2. The film of claim 1 wherein the side walls of said pyramid-shaped protuberances form an angle of between about 10 degrees to about 75 degrees to the plane of the film.

3. The film of claim 2 wherein said angle formed by said sidewall is about 45 degrees.

4. The embossed film of claim 1 wherein said length of the base of one of said protuberances is from about 4 mils to about 10 mils.

5. The film of claim 3 wherein the base of said pyramid is a rectangle.

6. The film of claim 5 wherein the base of said pyramid is a square.

7. The film of claim 1 wherein said protuberances have a base length of from about 4 mils to about 10 mils and a height of from about $\frac{1}{2}$ mil to about 4 mils.

* * * * *

UNITED STATES PATENT AND TRADEMARK OFFICE
CERTIFICATE OF CORRECTION

PATENT NO.   : 4,343,848
DATED        : August 10, 1982
INVENTOR(S)  : ERVING A. LEONARD, JR.

It is certified that error appears in the above-identified patent and that said Letters Patent is hereby corrected as shown below:

Column 1, line 28 reads "as low a surface gloss as possible to order to simulate"
should read --as low a surface gloss as possible in order to simulate--.

In The Claims:

Column 4, line 41 reads "tween about 10 degrees...."
should read --tween about 20 degrees....--.

Column 4, line 44 reads "said sidewall is about...."
should read --said sidewalls is about....--.

Figure 4:
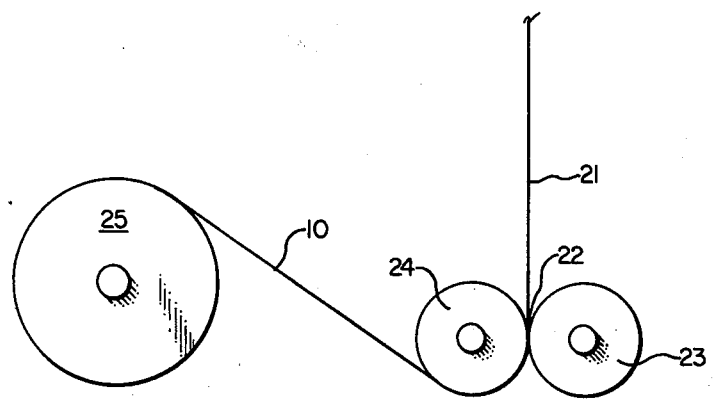

In The Drawings:

On Sheet 2, Fig. 4 should be deleted.

On Sheet 1, "Sheet 1 of 2" should read --Sheet 1 of 1--.

Signed and Sealed this

Eleventh Day of January 1983

[SEAL]

Attest:

GERALD J. MOSSINGHOFF

Attesting Officer   Commissioner of Patents and Trademarks